United States Patent [19]

Welch

[11] 4,060,405
[45] Nov. 29, 1977

[54] SELECTIVE HERBICIDE FOR EVERGREEN SEEDLINGS

[75] Inventor: Aaron Waddington Welch, Raleigh, N.C.

[73] Assignee: E. I. Du Pont de Nemours and Company, Wilmington, Del.

[21] Appl. No.: 607,897

[22] Filed: Aug. 26, 1975

[51] Int. Cl.$^2$ ............................................. A01N 9/22
[52] U.S. Cl. ....................................................... 71/93
[58] Field of Search ........................................... 71/93

[56] References Cited

U.S. PATENT DOCUMENTS 3,902,887  9/1975  Lin ......................................... 71/93

OTHER PUBLICATIONS

Fuchs et al, Ger. Offen. 2,326,312 Chem. Abst. vol. 80 (1974) 59971x.
Belkov et al. Chem. Abst. vol. 83 (1975) 142892e.
Velichko et al. Chem. Abst. vol. 76 (1972) 55134w.
Voeller et al. Chem. Abst. vol. 81 (1974) 59227e.

Primary Examiner—Lewis Gotts
Assistant Examiner—Catherine L. Mills

[57] ABSTRACT

1-Methyl-3-cyclohexyl-6-dimethylamino-s-triazine-2,4(1H,3H)-dione

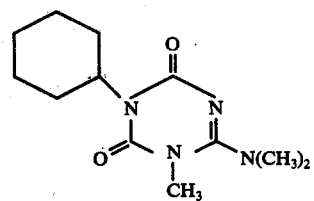

is useful for the selective control of many grassy weeds, broadleaved weeds, and weed trees in evergreen seedling stands.

8 Claims, No Drawings

SELECTIVE HERBICIDE FOR EVERGREEN SEEDLINGS

BACKGROUND OF THE INVENTION

1-Methyl-3-cyclohexyl-6-dimethylamino-s-triazine-2,4(1H,3H)-dione and its use as a broad spectrum herbicide are disclosed and claimed in copending U.S. patent application Ser. Nos. 476,553 and 476,552, now U.S. Pat. No. 3,902,887, both filed June 5, 1974, by Lin, both of which applications are divisions of U.S. patent application Ser. No. 348,321, filed Apr. 5, 1973, now abandoned, which is, in turn, a continuation-in-part of U.S. patent application Ser. No. 256,249, filed May 24, 1972 now abandoned.

The present invention results from the discovery that this compound exhibits a surprising selective herbicidal activity. That is, although this compound is known to be a potent broad spectrum industrial herbicide, it has unexpectedly been found that when applied under the proper conditions, it will effectively control many grassy weeds, broadleaved weeds, and broadleaved weed trees in evergreen seedling stands with safety to the evergreen seedlings.

SUMMARY OF THE INVENTION

This invention relates to the use of 1-methyl-3-cyclohexyl-6-dimethylamino-s-triazine-2,4(1H,3H)dione

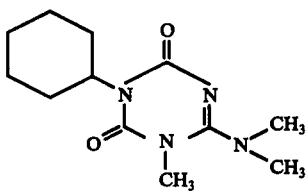

I as a selective herbicide in evergreen seedling stands. This compound can be applied either pre-emergence or post-emergence to effectively control a variety of grassy weeds, broadleaved weeds and weed trees in evergreen seedling stands with safety to these seedlings, i.e., application can be made pre-emergence to the locus of the evergreen seedlings within a few weeks prior to expected germination of the weed seeds or as a directed post-emergence application to the locus of the evergreen seedlings during the period of active growth of the weed species.

DESCRIPTION OF THE INVENTION

Synthesis of the compounds

The compound of formula I can be made by the processes described and exemplifed in U.S. patent application Ser. Nos. 476,553 and 476,552, identified above, and by the process described and exemplified in U.S. Pat. No. 3,850,924 granted Nov. 26, 1974 to Julius Fuchs and Joel B. Wommack.

In addition, the following preferred process, which is the subject of copending U.S. patent application Ser. No. 574,351, filed June 5, 1975 by Adams et al., can be used to prepare the compound of formula I:

Equation I represents preparation of the starting material as described in U.S. Pat. No. 3,657,443.

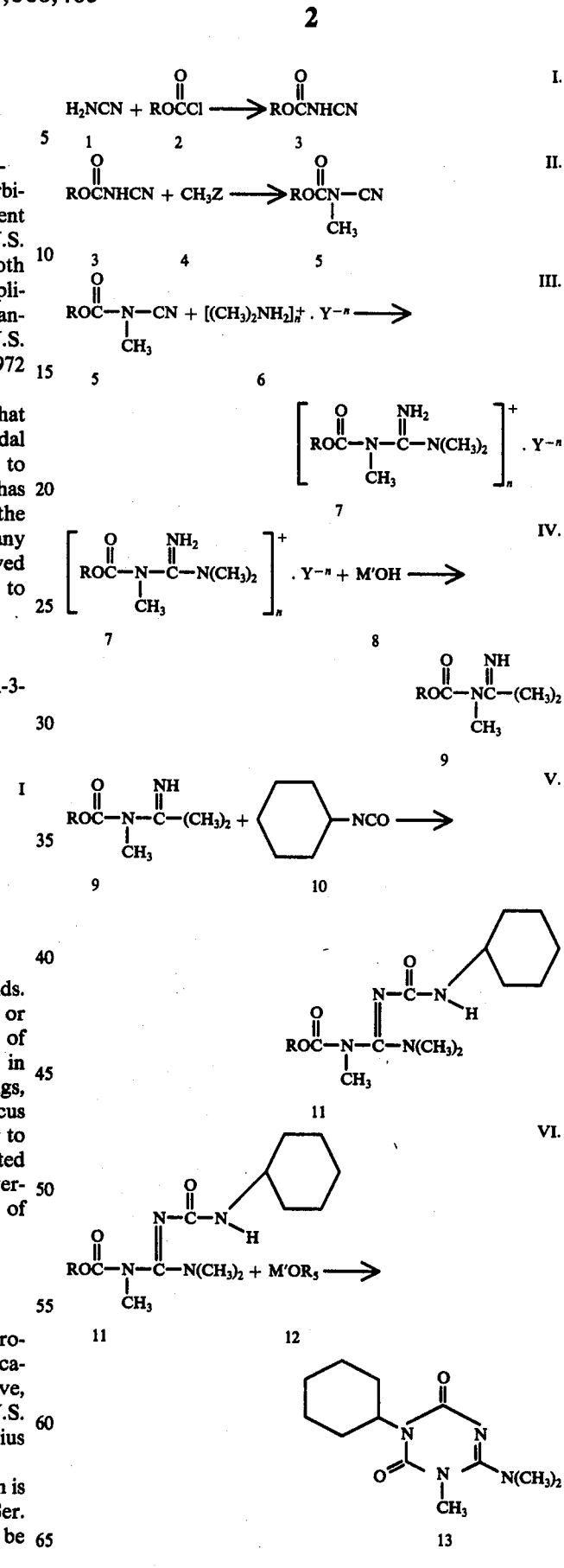

wherein
R is ethyl, n-propyl, or isopropyl;

Y is Cl⁻ or SO₄⁼; n = 1 when Y is Cl⁻ and n = 2 when Y is SO₄⁼;

Z is iodide, bromide or

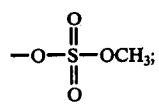

M' is alkali metal; and $R_5$ is hydrogen or alkyl of 1–4 carbon atoms.

Step I and II are performed sequentially in water. Compound 5 is isolated by separating it from the aqueous brine formed in these reactions.

After the reaction of step III is completed, compound 7 and any unreacted compound 6 must be converted to the free base forms with an alkali metal hydroxide. The untreated amine, $(CH_3)_2NH$, must be removed so that it will not be present in step V.

In the following detailed description, all temperatures are in degrees centigrade and all percentages are by weight unless otherwise stated.

An aqueous solution of the sodium salt of compound 3 containing from 15–35% of compound 3, preferably 20–30%, is reacted at 10°–70°, preferably 40°–45°, with 0.9–2.0, preferably 1.45–1.55 molecular equivalents of an alkylating agent 4 (for example, dimethyl sulfate) during a period of 1–16 hours, preferably 2–4 hours (equation II). Methyl iodide or bromide can be used instead of dimethyl sulfate; the sulfate is preferred for economic reasons.

As the reaction proceeds, a second phase of compound 5 forms. After the reaction has proceeded for the desired time, the upper layer is separated and the lower, aqueous, layer can be discarded, or if economic conditions justify, this layer can be extracted with an organic solvent, preferably toluene, or distilled to recover the small amount of compound 5 contained therein.

The upper layer is added to an aqueous solution containing 15–75% of the amine hydrochloride or 15–45% of the amine sulfate, compound 6, preferably 25–50% of the hydrochloride (equation III). The mole ratio of amine salt to compound 5 can be from 0.8–3, preferably 1.0–1.35. The mixture is then agitated for 0.5–6 hours at 50°–100°, preferably 85°–95° (equation III). Higher temperatures require shorter reaction time and vice versa. It is important to control the pH between 5.8 and 8.0 during reaction III. If the pH is too low, the reaction will be very slow; if the pH is too high, the product 7 will decompose. This control is most conveniently maintained by using electrodes to monitor the pH and adding base, for example, sodium hydroxide, potassium hydroxide, or calcium hydroxide as needed. Sodium hydroxide is preferred.

It should be realized that in these highly concentrated solutions, pH readings may be only coincidentally related to the hydrogen ion concentration. However, when the meters and electrodes are calibrated against a standard buffer before use, the pH response of the electrodes in the reaction mass indicates the state of the reaction.

The resulting reaction mass contains compound 7 and by-product tri-substituted guanidine as well as unreacted compound 6, all present as salts. Before proceeding with step V it is necessary to convert compound 7 into its free base, compound 9. This also converts unreacted compound 6 into free amine, $(CH_3)_2NH$ which is removed to prevent the formation of by-product ureas. This operation can be effected by adding 10–50% aqueous sodium hydroxide until the pH is 11.0 to 12.5 as determined by a glass electrode meter combination and extracting with an organic solvent. Distillation of a portion of the organic solvent used for extraction removes the more volatile amine, $(CH_3)_2NH$. The amine can also be removed directly from the aqueous alkaline solution by distillation. The former procedure is preferred.

The extraction procedure can be performed by passing the aqueous alkaline solution through a continuous counter-current extractor where the organic phase is a solvent such as methylene chloride, benzene, chlorobenzene, toluene, or xylene; toluene is preferred. A batchwise extraction can also be performed. Temperature can vary between 9° and 65° C. The amount of solvent can vary from 0.5 to 10 parts per part aqueous phase, depending on economic factors. The exit organic solvent is sent to a still where amine, $(CH_3)_2NH$, and any entrained water are distilled overhead, leaving a residual solution of compound 9. The concentration of compound 9 will, of course, depend on the operating parameters of the extractor and still.

The residual solution of compound 9 is analyzed by gas chromatography for tri-substituted guanidine and for compound 9. If any guanidine is present, a stoichiometric amount of 5–10% aqueous sulfuric or hydrochloric acid, preferably sulfuric, is added to form the salt of the guanidine.

Isocyanate 10 is now added. The amount added can vary from 0.8 to 1.0 moles of compound 10 per mole of compound 9; 0.90–0.98 is preferred. The resulting reaction mass is stirred at 10°–90° C., preferably 50°–75° C., until the reaction is complete. Reaction time can be from 0.5 to 8 hours.

If less than a stoichiometric amount of compound 10 has been added, the pH is adjusted to 5.5 by adding 5–10% sulfuric or hydrochloric acid; sulfuric is preferred. If acid has been added, the mixture is allowed to settle, and the layers are separated. The lower, aqueous, layer is recycled to the extraction step, and the upper layer is dried by distilling until a constant head temperature is attained either under vacuum or at atmospheric pressure; absolute pressure of 100 to 400 mm Hg is preferred.

If acid is not used, the reaction mass does not have to be distilled. The product 11 can be isolated by concentration and/or cooling of the solution until crystallization occurs followed by filtration or centrifugation. However, it is usually more convenient to carry it forward as a solution to the next step (equation VI).

Compound 9 is subject to decomposition in aqueous solution, particularly under conditions of temperature and pH. Under such conditions it tends to decompose into the corresponding tri-substituted guanidine as illustrated in the following equation:

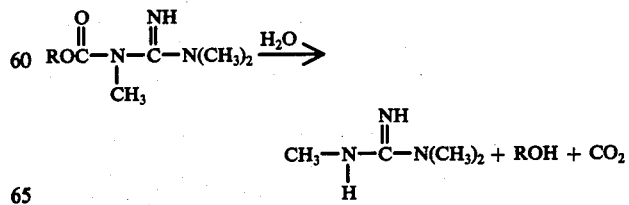

The rate of decomposition is directly proportional to the pH and temperature. Therefore, when removing amine, $(CH_3)_2NH$, by direct distillation from water, it is preferred to use a vacuum or inert gas to perform the operation as rapidly as possible.

The above-mentioned aqueous distillation procedure can be operated batch-wise or continuously. It is preferred to carry out the operation in a continuous manner so that the exposure of compound 9 to high temperature and high pH is reduced to a minimum. This is accomplished by adding aqueous alkali metal hydroxide to the product from step III in a pipeline reactor or by running the product and an alkali metal hydroxide into a small agitation vessel with a short hold-up time, no more than 10, preferably no more than 2 minutes. The separate flow rates are adjusted so that the resulting pH is between 11.0 and 13.0. If the concentration of amine salt used is such that alkali metal salt precipitates during this neutralization, additional water should be added to maintain this salt in solution. The overflow from this vessel is fed through a distillation column operated under vacuum. The column is heated by feeding steam into the bottom. Amine, $(CH_3)_2NH$, and water are taken off as distillate overhead and an aqueous solution of compound 9 and tri-substituted guanidine as bottoms.

The conditions under which the column can be operated are selected so that the temperature of the feed through the column is not over 50° C. This necessitates cooling the procuct from equation III to approximately 30° C before adding the caustic. The column is operated at an absolute pressure of 25–300 mm of mercury, preferably 50–150 mm, and the amount of steam fed to the bottom of the column is adjusted such that the amount of water taken overhead along with the amine is equivalent to 5–25% of the weight of the reaction mass from equation IV.

The bottoms from the above distillation are fed into a hold tank which is maintained at a pH of 5–7 by the continuous addition of either sulfuric or hydrochloric acid; hydrochloric is preferred. The concentration of compound 9 in the neutralized solution is maintained at 15–50%, preferably 20–40%. The concentration will depend upon the concentration of the aqueous solution of the amine, the concentration of the base and acid solutions employed in the previous steps, and the amount of concentration or dilution which occurred during the distillation. The temperature of this solution is maintained at 25°–45°, preferably 25°–35°, by either cooling the bottoms in a continuous-type cooler before neutralization or by cooling the neutralization vessel itself.

When the amine has been removed by direct distillation from water, step V is performed by preparing a mixture of the above solution and a solvent such as benzene, chlorobenzene, toluene, or xylene; toluene is preferred. The amount of solvent added should be sufficient to dissolve the amount of compound 11 which will be formed. Generally, the amount of solvent used is about 7–10 times the amount of compound 11 present in the aqueous solution.

An amount of compound 10 which is stoichiometrically equivalent to 85–100%, preferably 90–98%, of compound 9 present in the aqueous layer is now added in one portion or continuously for up to three hours, preferably 30 minutes to one hour and 50% aqueous caustic is added simultaneously with good agitation at a rate which will maintain the pH at 9–10, preferably 9.3–9.7. The caustic addition is continued until the pH is almost constant. The temperature is maintained at 10°–90° C., preferably 35°–50° C., during the addition by external heating and cooling as required. The caustic addition time is from 1–8 hours. The pH is then adjusted to 6.0 with acid. The agitation is stopped and the layers allowed to separate. The lower aqueous layer is removed and the upper organic layer is dried by distilling until a constant head temperature is attained either under vacuum or at atmospheric pressure; absolute pressure of 100–400 mm Hg is preferred.

The solution or slurry containing compound 11 is cooled if necessary to 25°–55° C while anhydrous free dimethylamine is added. It is preferred to add the amine at 25°–55° C, but higher or lower temperatures can be used depending on the solubility of the amine in the particular solvent. It is important to have at least 0.5, and preferably 1.0–8.0, moles of amine per mole of compound 11.

Next the ring closure catalyst (compound 12) is added (equation VI). The catalyst is an alkali metal alkoxide or hydroxide. Alkali metal alkoxides can be added either as dry solid or as a solution in the alkanol. Alkali metal hydroxides can be added as a solution in an alkanol. Dry sodium methoxide or a solution of sodium methoxide in methanol is a preferred catalyst. The amount of catalyst needed is from 0.1 to 5.0 mole percent of compound 11. Higher concentrations are not desirable because side reactions begin to intervene. A preferred concentration of compound 12 is from 2.0 to 4.0 mole percent of compound 11. The temperature is not critical and the ring closure reaction can proceed at temperatures from 0° to 120° provided that the amine is kept within the reaction system. The reaction is normally exothermic and the solution may be cooled if a lower temperature is required to retain the amine. It is critical that the amine remain present until ring closure is about complete.

After the catalyst is added, the reaction mass is held for 15 seconds to 2 hours to insure completion of the ring closure. The reaction is rapid and normally is about complete in less than 15 minutes. The more completely anhydrous the reaction mass, the more rapid is the reaction. An amount of acid equivalent in moles to the amount of the catalyst is added to the reaction mass after ring-closure is complete. This acid neutralizes the catalyst and/or reaction by-products which catalyze product decomposition during the isolation step. Preferably, the acid is added as soon as possible after ring-closure is complete. The type of acid, either organic or inorganic, is not critical; but organic acids are preferred, particularly acetic acid. The added amine, by-product alkanols, and part of the solvent are then removed by distillation either at atmospheric or reduced pressure.

Alternatively, the ring-closure reaction can be performed in a continuous manner. In this embodiment the catalyst is mixed with the reaction mass containing compound 11 and the amine in a pipeline reactor. The acid is added downstream after the temperature rise is complete. The amine, by-product alcohols and part of the solvent are then removed by distillation.

The residue is washed at 30°–100° C., preferably 50°–70° C., with 5% aqueous alkali metal hydroxide, preferably sodium hydroxide, in an amount equal to or slightly greater than (up to 20% molar excess) the amount of catalyst. The layers are allowed to settle, the aqueous layer is removed, and the organic layer is washed with water in an amount approximately equivalent in volume to the caustic wash. Again the layers are allowed to settle, the aqueous layer is removed, and the pH of the wet organic layer is adjusted to 6–7 with acid.

(The pH is measured using a glass-calomel combination electrode.) Organic acids are preferred for this operation; acetic acid is especially preferred. This washing procedure removes by-products formed during the ring-closure reaction. If a less pure product is satisfactory, the washing steps can be eliminated.

The product can be isolated from the organic solvent either after the washing operation or without washing concentrations of the organic phase by distillation which is then diluted with a poor solvent for compound 13, e.g., hexane, which causes compound 13 to precipitate. The stable crystalline product is recovered by conventional methods.

In the following examples, all parts are by weight and all temperatures in degrees centrigrade unless otherwise indicated.

EXAMPLE 1

A. Synthesis N-ethoxycarbonyl-N-methylcyanamide (Equations I and II)

657 Parts of ethyl chloroformate and 945 parts of a 50% aqueous sodium hydroxide solution were added simultaneously to a solution of 504 parts of a 50% aqueous cyanamide solution in 825 parts of water at 25° during a period of 90 minutes and at a pH of 6.9 to 7.1. As the addition of the reactants progressed, the temperature of the reaction mass was allowed to rise to 53°–55° and was maintained within that range by cooling. When the addition was complete, the reaction mass was cooled to 40°. Dimethylsulfate (1,134 parts) was then added during one hour with stirring while maintaining the pH at 7 to 7.1 by the addition of 50% aqueous sodium hydroxide solution. After holding 3 hours at 40° the resulting two-phase solution was transferred to a separatory funnel. The upper phase of N-ethoxycarbonyl-N-methylcyanamide was separated and the lower aqueous phase was sent to secondary recovery, either distillation or extraction. The upper phase of 669 parts was 93% N-ethoxycarbonyl-N-methylcyanamide (81% yield). This upper phase is usually pure enough for subsequent steps. However, vacuum distillation was used to provide pure N-ethoxycarbonyl-N-methylcyanamide, b.p. 67° at 2.2 mm.Hg.

B. Synthesis of N-ethoxycarbonyl-N,N',N'-trimethylguanidine (Equations III and IV)

A solution of 339 parts of dimethylamine hydrochloride in 500 parts of water was heated to 50° and 458 parts of the upper phase from (A) was added to it. The resulting two-phase mixture was then heated for approximately 2.25 hours at 90° and pH of 6.5, after which time the starting N-ethoxycarbonyl-N-methylcyanamide had nearly completely disappeared. The pH was kept at 6.5 by adding 50% sodium hydroxide as required. The solution was then cooled to 40° and 25% aqueous hydroxide solution was added to reach pH 11.5. Repeated extraction of the reaction solution with toluene and partial evaporation of the toluene gave a solution containing 489 parts of crude N-ethoxycarbonyl-N,N',N'-trimethylguanidine from which the pure product was isolated by distillation at 70°/0.3 mm.Hg.

C. Synthesis of Ethyl N-(N'-cyclohexylcarbamoyl-N,N-dimethylamidino)-N-methylcarbamate (Equation V)

11 Parts of cyclohexyl isocyanate was added to 16 parts of N-ethoxycarbonyl-N,N',N'-trimethylguanidine in 150 parts of toluene. The temperature was kept at 50° to 75° for 1.25 hours to complete reaction. The product, ethyl-N-(N-cyclohexylcarbamoyl-N',N'-dimethylamidino)-N-methylcarbamate was isolated by crystallization, filtration, and drying, m.p. 97°–98°. Preferably, however, it is kept as a toluene solution carried forward as such to the next step (Equation V).

D. Synthesis of 1-methyl-3-cyclohexyl-6-dimethylamino-s-triazine-2,4(1H,3H)dione (Equations II, III, IV, V)–

A 50% stoichiometric excess of dimethylsulfate (1234 parts) was added at 40° during one hour with agitation to 3141 parts of an aqueous solution containing 888 parts of the sodium salt of compound 3 (R = ethyl) which had been adjusted to pH 7 with 50% aqueous sodium hydroxide. The reaction was allowed to continue for 3 hours while the temperature was maintained at 40° by external heating or cooling and at pH 7 by the addition of 50% aqueoussodium hydroxide as required. During the reaction a separate phase of compound 5 (R = ethyl) was formed.

When the reaction was about complete, the agitation was stopped and the layers allowed to separate. The upper layer of 728 parts was 93% pure compound 5 (R = ethyl). It was separated and added to 1,200 parts of an aqueous solution containing 540 parts of dimethylammonium chloride. The resulting mixture was heated to 90° and stirred for 2.25 hours at pH 6.5. The pH was maintained at 6.5 by adding 50% sodium hydroxide as required. The solution was then fed into a mixing tee along with 25% aqueous sodium hydroxide. The separate feed rates were adjusted so that the effluent from the tee was kept at pH 11.0–11.5. The effluent from this vessel was fed into the top of a continuous counter-current extractor, which operates as a 5 theoretical plate column. Toluene was fed into the bottom of the column at a rate of 2.25 pounds of toluene per pound of aqueous feed. The toluene solution at the top of the column overflows into an amine stripper.

In the stripper, excess dimethylamine, entrained water, and some toluene solvent are distilled overhead through a packed column. The residual toluene solution of 7743 parts contained 777 parts of compound 9 (R = ethyl). Analysis showed by-product 1,1,3-trimethylguanidine to be present in this residue, and a small amount of sulfuric acid solution was added to exactly neutralized all the 1,1,3-trimethylguanidine but little or none of compound 9.

507 Parts of cyclohexylisocyanate was added to this residue. The mixture was then stirred at 50°–75° for 1.25 hours. It was cooled to 40° and sulfuric acid solution was added with good stirring until the pH of the aqueous phase was 5.5. The organic phase was separated and dried by brief azeotropic distillation at a pressure of 100 mm mercury. The organic phase of 8,200 parts contained 1,205 parts of compound 11 (R = ethyl).

Dimethylamine (1,095 parts) was added to the solution of compound 11 while the temperature was maintained at 25°–50° by external cooling. Then 35 parts of a 25% solution of sodium methoxide in methanol was added with good agitation. The reaction is slightly exothermic and the temperature increased 4° during 15–45 seconds. The reaction was allowed to continue for an additional two minutes; then 9.72 parts of acetic acid were added. The solution was then distilled until a constant 110° head temperature showed that dimethylamine and by-product alkanols have been completely removed. The still bottoms were cooled to 60° and washed with a small quantity of 5% sodium hydroxide followed by a small quantity of water. The amount of sodium hydroxide was calculated so that it was equivalent in moles to the acetic acid added earlier.

The toluene phase was then concentrated by distillation until the concentration of compound 13 ($R_1 =$ reached 50% by weight. The residue was cooled to 40° and stirred while n-hexane was added slowly.

The weight of n-hexane used was 80% of the total weight of the 50% solution. During the n-hexane addition the solution was seeded with compound 13. The crystals were recovered by filtration and dried to give 920 parts of compound 13 m.p. 112°–115° C.

Formulation and use of the compound

In beneficial forest land management, the elimination of vegetative growth on an area except for that of a limited number of arborescent species of commercial value becomes desirable. Very often, prospective forest sites are so completely covered with low-value or worthless vegetation that the desired tree species will not get a start at all. In other instances, the desired species are present but their growth is greatly restricted by a heavy population of undesirable plants. An herbicide that will kill competing plants without serious injury to valuable timber or pulp species is particularly needed by forest managers. In many areas, normal plant sucession leads away from the desired commercial species and a method of treatment such as that of the present invention is necessary to maintain production of useful timber and pulp wood.

Proper application of the compound of formula I will control undesired vegetation in stands of everevergreen seedlings, i.e., the compound of formula I can be used to control a variety of grassy weeds, broadleaved weeds and weed trees in evergreen seedling stands with safety to these seedlings. This safety applies particularly to various valuable species of pines (*Pinus spp.*), Douglas fir (*Pseduotsuga spp.*) and hemlock (*Tsuga spp.*).

The precise amount of compound to be used in any given situation will vary according to the time of treatment; the weed species and soil type involved the formulation used the mode of application, prevailing weather conditions, particularly rainfall foliage density and like factors. In addition, the particular evergreen seedling species should be taken into consideration. In any event, use rates necessary to provide effective control even with respect to many weed species that are resistant to other herbicides are relatively low. Since so many variables play a role, it is not possible to state the rate of application suitable for all situations. However, broadly speaking, compounds of this invention are used at levels of about 0.5 to about 12 kilograms of the active compound per hectare. A more preferred rate is in the range of about 1 to 10 kilograms per hectare, and the most preferred rate is about 2 to about 8 kilograms per hectare.

The application may be made pre-emergence or post-emergence to the weed plants to be controlled. Pre-emergence applications are most effective when made within a few weeks prior to expected germination of the weed species. Post-emergence applications are preferrably made during the period of active growth of the weed species. The applications may be made prior to the planting of the desirable tree species or to land on which they are already present. In the latter case, treatment is best applied either before or well after the period of most active growth of the crop trees. Successful applications may be made during the active growing season, however, if care is taken to avoid foliage. In all instances, the treatment should be applied uniformally.

Among the weeds and undesirable tree species controlled by application of the present method are fescue (*Festuca spp.*), panic grass (*Panicum spp.*), orchard grass (*Dactylis glomerata*), vaseygrass (*Paspalum urvillei*), quackgrass (*Agropyron repens*), broomsedge (*Andropogon virginicus*), sweet vernal grass (*Anthoxanthum odoratum*), bluegrass (*Poa spp.*) Bermudagrass (*Cynodon dactylon*), dallisgrass (*Paspalum dilatatum*), bracken fern (*Pteris aquilina*), common yarrow (*Achillea millefolium*), wild carrot (*Daucus carota*), horseweed (*Erigeron canadensis*), campion (*Silene stellata*), Canada thistle (*Cirsium arvense*), goldenrod (*Solidago spp.*), common ragweed (*Ambrosia artemisifolia*), ragwort (*Senecio spp.*), broom (*Cytisus spp.*) curly dock (*Rumex crispus*), honeysuckle (*Lonicera japonica*), brambles (*Rubus spp.*), wild grape (*Vitis spp.*), groundsel tree (*Baccharis halimifolia*), toetoe (*Cortaderia spp.*), persimmon (*Diospyros virginiana*), red maple (*Acer rubrum*), red gum (*Liquidambar styraciflua*), eucalyptus (*Eucalyptus regnans*), post oak (*Quercus stellata*), blackjack oak (*Quercus marilandica*), hackberry (*Celtis occidentalis*), and sassafras (*Sassafras variifolium*).

Among the valuable tree species that benefit from the method of this invention are: loblolly pine (*Pinus taeda*), longleaf pine (*Pinus palustris*), slash pine (*Pinus caribaea*), shortleaf pine (*Pinus echinata*), ponderosa pine (*Pinus ponderosa*), Austrian pine (*Pinus nigra*), Monterey pine (*Pinus radiata*), Douglas fir (*Pseudotsuga taxifolia*) and western hemlock (*Tsuga heterophylla*).

The compound of formula I can be used for weed control in evergreen seedlings either alone or in combination with other herbicides. An important function of the added herbicide is to prolong the period of weed control obtained. Compounds particularly effective for this purpose are diuron [3-(3,4-dichlorophenyl)-1,1-dimethylurea] and certain of the substituted triazines.

The compound of formula I can be formulated in the various ways which are conventional for herbicides of similar physical properties. Useful formulations include wettable and soluble powders, suspensions and solutions in solvents and oils, aqueous dispersions, dusts, granules, pellets, and high-strength compositions. Broadly speaking, these formulations consist essentially of about 1–99% by weight of herbicidally active material and at least one of a. about 0.2–20% by weight of surface active agent, and b. about 5–99% by weight of solid or liquid diluent. More specifically, the various types of formulations will generally contain these ingredients in the following approximate porportions:

| | PERCENT BY WEIGHT | | |
|---|---|---|---|
| | Herbicide | Diluent | Surfactant |
| Wettable Powders | 25–90 | 0–74 | 1–10 |
| Suspensions or Solutions | 5–50 | 40–95 | 0–10 |
| Aqueous Dispersions | 10–50 | 40–89 | 1–10 |
| Dusts | 1–25 | 70–99 | 0–5 |
| Granules and Pellets | 1–35 | 65–99 | 0–15 |
| High-Strength | | | |

-continued

| | PERCENT BY WEIGHT | | |
|---|---|---|---|
| | Herbicide | Diluent | Surfactant |
| Compositions | 90-99 | 0-10 | 0-2 |

The manner of making and using such herbicidal formulations is described in numerous patents. See, for example, Luckenbaugh, U.S. Pat. Nos. 3,309,192; 3,235,357; Todd, 2,655,445; Hamm et al., 2,863,752; Scherer et al., 3,079,244, Gysin et al., 2,891,855; and Barrous 2,642,354.

EXAMPLE II

| Solution | |
|---|---|
| 1-methyl-3-cyclohexyl-6-dimethyl-amino-s-triazine-2,4(1H,3H)-dione | 37% |
| ethylene glycol monobutylether | 35% |
| methanol | 9% |
| water | 19% |

The ingredients are combined and stirred to produce a solution which can be extended with water for spraying.

EXAMPLE III

| Wettable Powder | |
|---|---|
| 1-methyl-3-cyclohexyl-6-dimethyl-amino-s-triazine-2,4(1H,3H)-dione | 25% |
| diatomaceous earth | 71.5% |
| dioctyl sodium sulfosuccinate | 1.5% |
| low viscosity methyl cellulose | 2% |

The ingredients are throughly blended and passed through a hammer mill to produce particles mostly all below 100 microns.

The selective herbicidal activity of the compound of formula I in evergreen seedlings has been demonstrated in each of the following tests.

EXAMPLE IV

On April 11, 1-methyl-3-cyclohexyl-6-dimethylamino-s-triazine-2,4(1H,3H)dione was applied in North Carolina to a series of field plots supporting a cover of oak and pine trees as well as mixed low-ground cover. Trees were still dormant at the time of treatment. Use rates included were 4, 8 and 16 kg/ha of the active compound. The soils in the test area were a light sand. By September 11, virtually all of the groundcover plants and all of the trees except for loblolly pine had been killed at the lowest treatment level. The oak trees killed were post oak and blackjack oak. The pine trees had survived and remained in a healthy condition even on the plots treated at the 8 kilogram rate.

EXAMPLE V 1-methyl-3-cyclohexyl-6-dimethylamino-s-triazine-2,4(1H,3H)dione was applied at the rate 1 kg/ha to nursery flats of silt loam soil that had previously been seeded with Douglas fir and a selection of weeds including ryegrass, mustard, pigweed and chickweed. The chemical application was made prior to the emergence of any of the plants. This treatment killed all of the representative weeds but allowed the normal development of the Douglas fir.

EXAMPLE VI

A test area in Texas covered with a stand of persimmon, pine and groundsel tree, as well as a variety of low-growing plants was selected. Random plots were treated with 1-methyl-3-cyclohexyl-6-dimethylamino-s-triazine-2,4(1H,3H)dione at rates of 4, 8 and 16 kg/ha. The chemical was applied on May 24 with a solid-stream single nozzle directed in such a way as to reach the soil with a minimum of foliage contact. By September 27, (after 68 cm of rainfall), the 4 kilogram rate had provided effects noted below on the undesired plant species:

| Plant Species | Percent kill by September 27 |
|---|---|
| Persimmon | 92 |
| Groundsel tree | 100 |
| Honeysuckle | 90 |
| Blackberry | 100 |
| Vaseygrass | 100 |
| Bermudagrass | 100 |
| Sunflower | 100 |

Pine, on the other hand, was not killed even at the rate of 8 kg/ha. In September of the following year, weed control remained excellent and the pine continued to thrive.

EXAMPLE VII

In New Zealand, 1-methyl-3-cyclohexyl-6-dimethylamino-s-triazine-2,4(1H,3H)dione was applied in February at rates of 8 and 12 kg/ha to field plots supporting toetoe and bracken fern. Control of both weed species was obtained at the lower use rate. In May, 1-year old seedlings of *Pinus radiata* were planted in the treated plots. The pine showed no phytotoxicity symptom.

EXAMPLE VII

In July, in New Zealand, newly planted seedlings of *Pinus radiata* and *Eucalyptus regnans* were treated with overall sprays of 1-methyl-3-cyclohexyl-6-dimethylamino-s-triazine-2,4(1H,3H)-dione at rates of 1, 2 and 4 kg/ha. All eucalyptus plants died. Pine, on the other hand, showed no adverse effect at the 1 and 2 kilogram rates and only a slight yellowing at the 4 kilogram level.

EXAMPLE IX

One-year old seedlings of *Pinus radiata* in New Zealand were treated in October, two months after planting, with 1-methyl-3-cyclohexyl-6-dimethylamino-s-triazine-2,4(1H,3H)dione at rates of 2, 4 and 8 kg/ha. Subsequent growth measurements indicated that all rates of treatment improved the growth of the pine seedlings due to control of the competing vegetation.

EXAMPLE X

Broadcast treatments with 1-methyl-3-cyclohexyl-6-dimethylamino-s-triazine-2,4(1H,3H)-dione at the rate of 3 kg/ha were made in April to field plots in Georgia. Five months after treatment, broomsedge had been killed whereas loblolly pine was uninjured. Rainfall during this exposure period was about 40 cm.

EXAMPLE XI

In April in North Carolina, directed sprays (sprays directed to the soil) of 1-methyl-3-cyclohexyl-6-dimethylamino-s-triazine-2,4(1H,3H)dione were applied to 4-year old loblolly pine trees. Rates used were 1,2,4 and 8 hg/ha. By June, weed plants including sumac and red gum had been seriously injured at the 2 kilogram rate. The pine, on the other hand, was thriving on the 4 kilogram plots and remained alive even in the 8 kilogram treatments.

EXAMPLE XII

In another North Carolina field test, overall applications of the compound were made to loblolly pine transplants three months after they had been set. Use rates were 1,2 and 4 kg/ha. About two months after treatment, all use rates had provided 80% or more control of a mixed weed population with excellent survival of the pine. Additionally, the pines on the treated plots were thriving especially well due to release from competition.

EXAMPLE XII

Applications of the compound of formula I at rates of 1, 2, and 3 kg/ha were made to Austrian pine in April near Olympia, Washington. The treatments were applied directly over the pines which were about 30 cm tall. Although groundsel was controlled at all rates, the pine trees showed no adverse effects.

EXAMPLE XIII

In the Pacific Northwest, 2 kg/ha of 1-methyl-3-cyclohexyl-6-dimethylamino-s-triazine-2,4(1H,3H)dione provided commercially acceptable control (80–85%) of quackgrass, sedges, bramble and Canada thistle. Seedling Douglas fir planted about two weeks after these treatments tolerated as much as 6 kg/ha of the herbicide. Douglas fir trees 1 to 3 meters tall were treated over the top with similar margin of safety.

I claim:

1. Method for preventing and controlling undesired vegetation in the locus of evergreen seedlings without causing significant injury to said seedlings comprising applying to the locus of said seedlings an effective amount of 1-methyl-3-cyclohexyl-6-dimethylamino-s-triazine-2,4(1H, 3H)dione.

2. Method of claim 1 wherein the triazine is applied at a rate of 0.5 to 12.0 kilograms per hectare.

3. Method of claim 1 wherein the triazine is applied at a rate of 2 to 8 kilograms per hectare.

4. Method of claim 1 wherein the triazine is applied pre-emergence with respect to the undesired vegetation.

5. Method of claim 1 wherein the triazine is applied post-emergence at a time other than during the active growing season of the pine seedlings.

6. Method of claim 1 wherein the evergreen seedlings are pines.

7. Method of claim 1 wherein the evergreen seedlings are Douglas fir.

8. Method of claim 1 wherein the evergreen seedlings are hemlock.

* * * * *